United States Patent [19]

Feucht et al.

[11] Patent Number: 4,770,173
[45] Date of Patent: Sep. 13, 1988

[54] MULTIPLE ELEMENT FLAT ELECTRODE USEFUL FOR HF-SURGERY

[75] Inventors: Peter Feucht, Berlin; Uwe Hagen, Forchheim; Hans-Juergen Meyer, Erlangen; Udo Redler, Effeltrich, all of Fed. Rep. of Germany

[73] Assignee: Siemens Aktiengesellschaft, Berlin and Munich, Fed. Rep. of Germany

[21] Appl. No.: 35,690

[22] Filed: Apr. 7, 1987

[30] Foreign Application Priority Data

Jul. 10, 1986 [DE] Fed. Rep. of Germany ....... 3623293

[51] Int. Cl.⁴ .............................................. A61B 17/39
[52] U.S. Cl. .................. 128/303.13; 128/798
[58] Field of Search ...................... 128/303.13, 303.14, 128/303.11, 639, 640, 644, 798, 802, 803

[56] References Cited

U.S. PATENT DOCUMENTS

| | | | |
|---|---|---|---|
| 3,699,968 | 10/1972 | Bolduc | 128/303.13 |
| 3,720,209 | 3/1973 | Bolduc | 128/798 X |
| 4,082,087 | 4/1978 | Howson | 128/640 |
| 4,088,133 | 6/1978 | Twentier | 128/303.13 |
| 4,381,789 | 5/1983 | Naser et al. | 128/798 |
| 4,494,541 | 1/1985 | Archibald | 128/303.13 |

FOREIGN PATENT DOCUMENTS

| | | |
|---|---|---|
| 0193173 | 9/1986 | European Pat. Off. . |
| 1087222 | 8/1960 | Fed. Rep. of Germany . |
| 1139927 | 11/1962 | Fed. Rep. of Germany . |
| 2414584 | 10/1975 | Fed. Rep. of Germany ........... 128/303.13 |
| 2849422 | 5/1979 | Fed. Rep. of Germany . |
| 8205363 | 9/1985 | Fed. Rep. of Germany . |
| 94867 | 1/1970 | France . |
| 2414812 | 9/1979 | France ........................... 128/303.13 |

Primary Examiner—Lee S. Cohen
Attorney, Agent, or Firm—Lawrence C. Edelman

[57] ABSTRACT

A multi-element electrode comprises at least two flat partial electrodes which are arranged in juxtaposition to a pre-established direction. To simplify the fabrication of such an electrode and in particular to allow the use of cable conductors of equal length for attachment thereto, provision is made for the two partial electrodes to exhibit facing edges which are at an angle to the pre-established direction. Such a construction is advantageous in the case of a three-part electrode. The electrode is preferably the neutral electrode of an HF-surgical apparatus.

17 Claims, 1 Drawing Sheet

MULTIPLE ELEMENT FLAT ELECTRODE USEFUL FOR HF-SURGERY

BACKGROUND OF THE INVENTION

1. Field of the Invention

The invention relates to an electrode having at least two partial electrode elements, in particular a neutral electrode for HF-surgery (i.e., High-Freguency electrosurgery), in which the partial electrodes are arranged in juxtaposition in a pre-established direction.

2. Description of the Prior Art

A neutral electrode of the above-mentioned type operates with two flat electrodes, as described in German Registered Design Patent GM No. 82 05 363, In this neutral electrode the electrical contact with the patient is monitored by means of a control circuit through which a low frequency control current flows. This control current flows from the contact surface of one partial electrode, through the skin of the patient, to the contact surface of the other partial electrode.

Another two element neutral electrode is described in German Patent Publication DE-OS No. 28 49 422.

Single element neutral electrodes are also employed in the present state of the art. HF-surgical apparatuses are frequently equipped with a monitoring circuit through which a check may be made to determine whether the single element electrode is in fact present in the circuit, i.e. is connected. For this purpose, a first and a second connecting lead is attached to the surface of the single element electrode. A control current is sent from the first connecting lead through the neutral electrode and the second connecting lead. If this control current exceeds a pre-established threshold, assurance is gained that the single element electrode is in fact present and does not have a defective electrical connection and/or has not become disconnected. The construction of the neutral electrode proposed herein is, in particular, to be capable of working in combination with a monitoring circuit of this type.

It has been demonstrated that a multi-element construction of the neutral electrode is also desirable, when an indication is to be provided by a monitoring circuit of whether such a neutral electrode makes large surface area contact or just a spot contact with the patient during the surgical procedure. Such a monitoring circuit is described in U.S. patent application Ser. No. 929,561, filed Nov. 10, 1986 and titled "Method and Apparatus for Monitoring the Surface Contact of a Neutral Electrode of an HF-Surgical Apparatus".

In the construction of a neutral electrode, every effort must be made to design it in such a way that good surface contact with the patient is assured. In the case of two element electrodes (i.e., two partial electrodes), this has previously resulted in a rectangular shape. If the two partial electrodes are arranged in juxtaposition in a pre-established direction, and if the connecting cable conductor is led to the electrode in this pre-established direction, a condition results where the conductor or lead for one of the partial electrodes must be longer than that for the other of the partial electrodes. This requires particular care in the fabrication of the neutral electrode in order that no interchange of the conducting leads can occur. Moreover, conductors of different length must be kept on hand.

An object of the present invention is to construct a multi-element electrode that will allow for simpler fabrication. In particular, assurance is to be provided that conductors of equal length may be connected to the partial electrodes.

SUMMARY OF THE INVENTION

The object is achieved according to the invention in that two partial electrodes exhibit edges facing one another at an angle to a pre-established direction.

With this construction it is possible to connect conductors of equal length to both of the partial electrodes. The fabrication is thereby simplified as well as the guidance of the conductors.

This construction results in particular advantage when a three element electrode is used. In such a construction three partial electrodes are provided. Two of the partial electrodes have an essentially trapezoidal shape and one is essentially rectangular. The three partial electrodes are arranged in juxtaposition in a pre-established direction and thereby form an essentially rectangular bearing surface having two short parallel sides, and two long parallel sides. An electrical termination is provided on that short side which is adjacent to the rectangular partial electrode.

The two partial electrodes having the facing angular edges (i.e., those of trapezoidal shape) may to advantage have equal surface areas and be of identical shape. This simplifies their fabrication, as well as stock-keeping.

It has been found, in the case of rectangular shaped single-element electrodes, that the four corners do not, as a rule, make especially good contact with the patient. This also applies to the outer four corners of a multi-element electrode. In order to assure an adequate contact surface in such cases, provision is made in the three element construction for the two outer partial electrodes to have somewhat larger surface areas than the surface area of the middle partial electrode. In particular they should be approximately 10% to 20% larger in order to achieve comparable results during measurement.

These and other features and advantages of the invention will be apparent from the following description of the preferred embodiments, and from the claims.

For a fuller understanding of the present invention, reference should now be made to the following description of preferred embodiments of the invention and to the accompanying drawings.

DETAILED DESCRIPTION OF THE INVENTION

Figure 1:
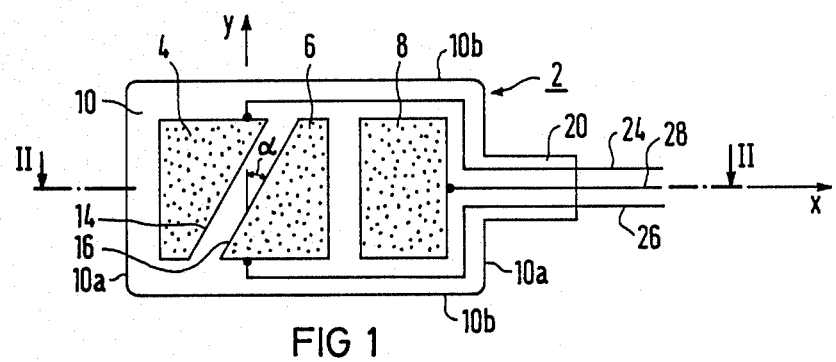
FIG. 1 illustrates a top view of a three element neutral electrode for an HF-surgical apparatus.
Figure 2:
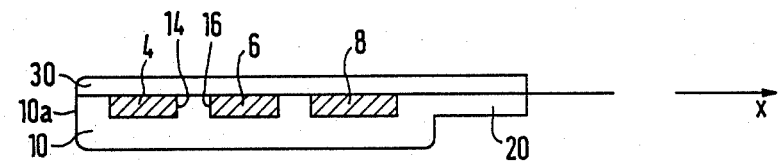
FIG. 2 illustrates a cross-section of the electrode shown in FIG. 1.

As shown in FIGS. 1 and 2, a neutral electrode 2 for HF-surgical apparatus comprises three flat surface partial electrodes 4, 6 and 8 of which two respective electrodes 4, 6 and 6,8 are separated from each other by an insulated strip having low electrical conductivity. The three partial electrodes 4, 6, 8 are arranged in juxtaposition e.g., lined up or located adjacent each other, in a pre-established direction x. They comprise a metal foil or a metal grid and are attached to a flexible base 10. Base 10, which is preferably made to be self-bonding or self-adhesive, is essentially rectangular in shape, longer in the x-direction than in the y-direction, and its edges extend past the edges of the three partial electrodes 4, 6 and 8. Base 10 has two sides 10a which are shorter than and perpendicular to two sides 10b, which sides 10b lie parallel to the x-direction.

Partial electrodes 4 and 6 are essentially of trapezoidal shape and partial electrode 8 is essentially of rectangular shape. It is to be noted that the length of the side of electrode 8 which is parallel to the x-direction is somewhat shorter than the length of the side parallel to the y-direction. It is to be further noted that partial electrodes 4 and 6 exhibit facing edges 14 and 16 respectively, extending at an angle $(90° - \alpha)$ with alpha not equal to 0°, 90° to the pre-established x-direction. The edges 14 and 16 run parallel to each other and form one of the insulated strips. It should be noted that in the interest of clarity and contrary to the scale shown in FIG. 1, edges 14 and 16 of two partial electrodes 4 and 6 are at an angle (alpha) of only a few degrees with respect to the perpendicular of the pre-established x-direction (i.e. the y-direction). This angle alpha may in particular be less than 10 degrees. It is also to be stressed that the insulated strips between the partial electrodes are actually substantially narrower than are illustrated, in the interest of clarity.

As shown in FIGS. 1 and 2, the juxtaposed arrangement of partial electrodes 4, 6, 8 results in an essentially rectangular conductive contacting surface assembly with two short and two long parallel sides, lying parallel to sides 10a and 10b, respectively. Thus, the two long sides run parallel to the pre-established x-direction.

Base 10 is provided with a small end-piece or electrical terminal 20 on the side of rectangular base 10 which lies adjacent to partial electrode 8. Electrical terminal 20 contains three connecting leads 24, 26 and 28 for partial electrodes 4, 6, and 8 respectively. Terminal 20 is located approximately in the middle of short side 10a. As shown, conductors 24 and 26 each run adjacent to one of the long sides 10b of base 10 and are connected adjacent said long sides 10b to the two trapezoidal partial electrodes 4 and 6, respectively. The points of connection are aligned with the y-axis. It is therefore possible to make connecting leads 24 and 26 of equal length, which simplifies the fabrication and lowers the cost of stock-keeping. Connecting lead 28 is shorter than connecting leads 24 and 26 and is in electrical contact with the outer edge of partial electrode 8 at its intersection with the x-axis.

As shown in FIGS. 1 and 2, it is possible to arrange partial electrodes 4 and 6 to have angular edges 14 and 16 in order to have equal surface areas. This has the advantage that identical partial electrode elements may be used during fabrication so that faulty construction due to changing one for the other is impossible. In contrast, it is also possible to arrange for at least one of the outer electrodes 4 or 8 to be formed with a larger surface area than middle electrode 6. In particular, the outer partial electrode 4 or 8 can be some 10% to 20% larger than middle partial electrode 6. Such a construction has the advantage that the contact surface of those partial electrodes that form the four corner points of the essentially rectangular surface are enlarged, so that a separation from the patient at these corner points—occasionally unavoidable—does not lead to undesirable consequences.

It has already been pointed out that partial electrodes 4, 6 and 8 may be composed of a net or grid of good electrically conducting material. These nets are applied to a base 10 that is made of a rubberized layer. For monitoring electrode 2 for good surface contact, it is advantageous to make this rubberized layer of an electrically conducting rubber. Base 10, electrodes 4, 6 and 8 and terminal 20 are suitably overlaid with a covering 30 that may be cemented on.

Terminal 20 may suitably comprise three adjacent contacts (not shown) to which a clamp of the alligator type may be connected. This means facilitates a rapid attachment of the side of electrode 2 having covering 30 to the patient and rapid contact positioning is possible.

Figure 3:
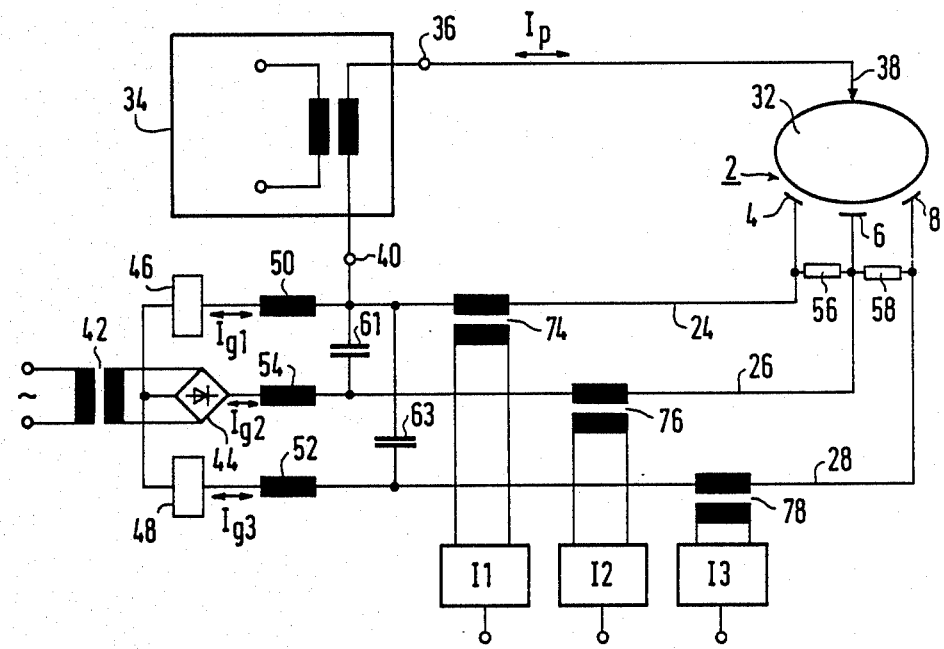
FIG. 3 illustrates a monitoring circuit applied to a three-element neutral electrode.

FIG. 3 illustrates a portion of a monitoring circuit which generates a test current Ip. By means of test current Ip, the contact of the neutral electrode 2 to the patient 32, or where necessary, the separation of the electrode 2, may be ascertained. For example, a separate HF-generator 34 in the HF-surgical apparatus may be employed for this purpose. As an alternative, the operating current of the HF-surgical apparatus may also be employed.

Here, as illustrated, HF-generator 34 is employed to provide the operating current. Generator 34 has a terminal 36 for connection to an active electrode 38 and an additional terminal 40 for connection to neutral electrode 2. Neutral electrode 2 is attached to patient 32 in a suitable manner during the surgical procedure, e.g., to the upper thigh. The surgeon controls active electrode 38 during the surgical procedure and undertakes specific incisions and coagulations.

Sufficiency of connection contact of neutral electrode 2 may also be monitored with a low frequency test current or, as shown here, with branching d.c test currents $Ig_1$ and $Ig_3$. Test currents $Ig_1$ and $Ig_3$ are obtained from the output of a low frequency transformer 42 which currents are rectified via rectifier 44 and directed to partial electrodes 4 and 8 of neutral electrode 2 via relays 46 and 48, HF chokes 50 and 52, through resistances 56 and 58 to middle electrode 6 and finally returned through a HF-choke 54 back to rectifier 44. Resistances 56 and 58 are formed by the effect of the strip of conductive rubberized layer 10 which separates the partial electrodes from each other. In an adequate contact of neutral electrode 2, relays 46 and 48 are energized. When neutral electrode 2 is detached, relays 46 and 48 activate an alarm system in the normal manner and/or actuate a safety means.

Connecting leads 26 and 28 are connected to terminal 40 via capacitors 61 and 63. Connecting lead 24 is directly connected to terminal 40. Current measuring devices 74, 76 and 78 are arranged in connecting leads 24, 26, 28, respectively. These are preferably of identical construction. They are in the form of current transformers in the present invention and serve as a means of measuring the three partial currents I1, I2, I3. The evaluation of these three partial currents I1, I2, I3 can follow, in the manner more fully described in the previously noted U.S. patent application Ser. No. 929,561.

Thus, there has been shown and described novel apparatus for a neutral electrode which fulfills all the objects and advantages sought therefore. Many changes, modifications, variations and other uses and applications of the subject invention will, however, become apparent to those skilled in the art after considering this specification and the accompanying drawings which disclose a preferred embodiment thereof. For example, the presently described principle of the partial electrodes 4 and 6 with edges 14 and 16 at an angle to the y-direction is applicable to standard electrodes, which as a rule are re-usable, as well as to electrodes that are designed to be disposable items.

All such changes, modifications, variations and other uses and applications which do not depart from the spirit and scope of the invention are deemed to be covered by the invention which is limited only by the claims which follow.

What we claim is:

1. An electrode particularly useful as a neutral electrode for an HF-surgical apparatus, comprising:
   at least three partial electrodes arranged in juxtaposition in a pre-established direction on a common base;
   two of said partial electrodes being essentially trapezoidal in shape and one being essentially rectangular in shape, said three electrodes being arranged in juxtaposition to each other in said pre-established direction so as to thereby form an essentially rectangular supporting surface having two short parallel and two long parallel sides, said two essentially trapezoidal partial electrodes exhibiting two facing edges which are at an angle to said pre-established direction and;
   an electrical terminal provided on the one side of said short sides which lies adjacent to said rectangular one of said three partial electrodes, said terminal containing three conductors, each conductor terminating at one of said three partial electrodes, wherein the conductors terminating at said trapezoidally-shaped electrodes are of equal length.

2. An electrode according to claim 1, wherein said electrical terminal is arranged to be located approximately in the middle of said one short side.

3. An electrode according to claim 2, wherein first and second ones of said conductors lie adjacent to and outward of said long sides of said supporting surface and are connected between respective ones of said trapezoidal partial electrodes and said electrical terminal.

4. An electrode according to claim 3, wherein said two facing edges of said partial electrodes make a given angle of only a few degrees with respect to an axis which is perpendicular to said pre-established direction.

5. An electrode according to claim 4, wherein said given angle is less than 10 degrees.

6. An electrode according to claim 1, wherein of said three juxtaposed partial electrodes, at least one end partial electrode has a surface area which is greater than the surface area of the partial electrode which lies in the middle of the end partial electrodes.

7. An electrode according to claim 6, wherein said at least one end partial electrode is 10% to 20% larger than said middle partial electrode.

8. An electrode according to claim 1, wherein said electrical terminal comprises at least two contacts lying adjacent one another to which a clamp in the form of an alligator clip may be connected.

9. An electrode according to claim 1, wherein said facing edges of said trapezoidal partial electrodes make a given angle of only a few degrees with respect to an axis which is perpendicular to said pre-established direction.

10. An electrode according to claim 9, wherein said given angle is less than 10 degrees.

11. An electrode according to claim 1, wherein said two trapezoidal partial electrodes have equal surface areas.

12. An electrode according to claim 11, wherein of said three juxtoposed partial electrodes, at least one of the end partial electrodes has a surface area which is greater than the surface area of the partial electrode lying in the middle.

13. An electrode according to claim 12, wherein said end partial electrode is 10% to 20% larger than said partial electrode lying in the middle.

14. An electrode according to claim 13, wherein said three partial electrodes comprise a grid of electrically conducting material which is attached to said common base.

15. An electrode according to claim 14, wherein said common base is an electrically conductive rubber.

16. An electrode particularly useful as a neutral electrode for an HF-surgical apparatus, comprising:
   an essentially rectangularly shaped base having long and short adjacent sides;
   at least two partial electrodes arranged in juxtaposition on said base in the direction of said long sides;
   said two partial electrodes exhibiting two facing edges which are at an angle to the direction of said long sides; and
   conductors connected to said two partial electrodes which are of equal length.

17. An electrode particularly useful as a neutral electrode for an HF-surgical apparatus, comprising:
   an essentially rectangular base having short and long adjacent sides;
   three partial electrodes arranged in juxtaposition on said base in the direction of said long sides;
   two of said partial electrodes being essentially trapezoidal in shape and one being essentially rectangular in shape, said three electrodes being arranged in juxtaposition to each other so as to thereby form an essentially rectangular supporting surface having two short parallel and two long parallel sides; and
   an electrical terminal is provided on the one of said short sides of said supporting surface which lies adjacent to said rectangular one of said three partial electrodes, said terminal containing one end of each three conductors, the other end of each conductor terminating at one of said three partial electrodes, the conductors terminating at said trapedzoidally-shaped electrodes being of equal length.

* * * * *